US000001509H

United States Statutory Invention Registration [19]

[11] Reg. Number: H1509

Eran et al.

[45] Published: Dec. 5, 1995

[54] HEPARIN ENHANCED PROCESS FOR SEPARATING ANTIHEMOPHILIC FACTOR (FACTOR VIII) AND FIBRONECTIN FROM CRYOPRECIPITATE

[76] Inventors: Harutyun Eran, 17135 - 2 Roscoe Blvd., Northridge, Calif. 91325; Duk S. Hwang, 2060 Empress Ave., South Pasadena, Calif. 91030; David P. Kosow, 525 N. Canyon Blvd., Monrovia, Calif. 91016

[21] Appl. No.: 71,600

[22] Filed: Jun. 4, 1993

Related U.S. Application Data

[60] Continuation of Ser. No. 779,937, Oct. 21, 1991, abandoned, which is a division of Ser. No. 363,968, Jun. 9, 1989, abandoned.

[51] Int. Cl.[6] ..... A61K 35/14; A61K 37/00

[52] U.S. Cl. ..... 530/383; 530/381; 530/386; 424/530

[58] Field of Search ..... 424/530; 514/802; 530/381, 383, 386

[56] References Cited

U.S. PATENT DOCUMENTS

| | | | |
|---|---|---|---|
| Re. 29,698 | 7/1978 | Fekete et al. | 260/112 |
| 2,847,348 | 8/1958 | Singher et al. | 167/74 |
| 3,560,475 | 2/1971 | Fekete et al. | 260/112 |
| 3,631,018 | 12/1971 | Shanbrom et al. | 260/112 |
| 3,652,530 | 3/1972 | Johnson et al. | 260/112 |
| 3,803,115 | 4/1974 | Fekete et al. | 260/112 |
| 4,086,218 | 4/1978 | Shanbrom et al. | 260/112 |
| 4,203,891 | 5/1980 | Rock | 260/112 |
| 4,210,580 | 7/1980 | Amrani | 260/112 B |
| 4,289,691 | 9/1981 | Rock | 260/112 |
| 4,305,871 | 12/1981 | Shanbrom | 260/112 |
| 4,383,989 | 5/1983 | Rock | 260/112 |
| 4,397,841 | 8/1983 | Johnson | 260/112 |
| 4,424,206 | 1/1984 | Ohmura et al. | 424/101 |
| 4,490,361 | 12/1984 | Heldebrant | 424/101 |
| 4,540,573 | 9/1985 | Neurath et al. | 424/85 |
| 4,543,210 | 9/1985 | Mitra et al. | 260/112 B |
| 4,613,501 | 9/1986 | Horowitz | 424/101 |
| 4,743,680 | 5/1988 | Mathews et al. | 530/383 |
| 4,789,733 | 12/1988 | Winkelman | 530/383 |

FOREIGN PATENT DOCUMENTS 511716X 4/1982 Spain .

OTHER PUBLICATIONS

Blomback et al, "Studies on Thrombin Inactivation in Normal Plasma, Serum, and Plasma Fractions, and its Relation to Heparin," Thrombosis et Diathesis Haemorrhagica, vol. IX, No. 3/4, pp. 368–386.

Preston, A. E., "The Factor VIII Activity in Fresh and Stored Plasma," British Journal of Haematology, vol. 13, No. 1, pp. 42–59 (Jan. 1967).

Engelberg, "Plasma Heparin Levels in Normal Man," Circulation, vol. XXIII, Apr. 1961, pp. 578–581.

Blomback et al, "On the Preparation of Human Antihaemophilic Globulin," Proc. 7th Congr. Europ. Soc. Haemat., London, 1959; Part II, pp. 587–593, (1960).

Mayer et al, Chemical Abstracts, vol. 56, 1962, 7847i.

Menitove et al, "Evaluation of Factor III–Rich Cryoprecipitate and the Plasma Fibronectin–Rich, Heparin–Precipitable Fraction Prepared from Single–Donor Plasma Units", Transfusion, vol. 27, No. 6 (1987).

Blumenstock et al, "Progressive Loss of Fibronectin–Mediated Opsonic Activity in Plasma Cryoprecipitate with Storage," Vox Sang., 54:129–139, (1988).

Bastida et al, "Fibronectin Is Required for Platelet Adhesion and For Thrombus Formation on Subendothelium and Collagen Surfaces," Blood, vol. 70, No. 5, pp. 1437–1442 (1987).

Letter to the Editor, "Fibronectin as Possible Adjunct in Treatment of Severe Malnutrition," The Lancet, pp. 962, Oct. 24, 1987.

*Primary Examiner*—Shean Wu

[57] ABSTRACT

A process is provided for preparing fibronectin and antihemophilic factor (Factor VIII) concentrates from a blood plasma cryoprecipitate.

13 Claims, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

FLOW CHART

HEPARIN-ENHANCED PROCESS - FIBRONECTIN

FLOW CHART

HEPARIN-ENHANCED PROCESS - FACTOR VIII

HEPARIN ENHANCED PROCESS FOR SEPARATING ANTIHEMOPHILIC FACTOR (FACTOR VIII) AND FIBRONECTIN FROM CRYOPRECIPITATE

This is a continuation of application Ser. No. 07/779/937, filed Oct. 21, 1991 now abandoned, which is a division of application Ser. No. 07/363,968 filed Jun. 9, 1989, now abandoned.

FIELD OF THE INVENTION

This invention relates to an improved process for preparing fibronectin and antihemophilic factor (Factor VIII) concentrates from blood plasma cryoprecipitate.

BACKGROUND OF THE INVENTION

Blood is made up of red blood cells (erythrocytes) carried in a solution called "plasma." Blood plasma includes numerous proteins which are useful for treating humans for various medical indications. Two examples of such proteins are fibronectin, also known as cold-insoluble globulin (CIg) and anti-hemophilic factor (AHF or Factor VIII).

Fibronectin is a multi-functional glycoprotein present in plasma at a concentration of approximately 300 micrograms per milliliter. Some of its biological properties include adhesion of cells to surfaces and binding to collagen, fibrin, and heparin. Reduced levels of fibronectin have been found in patients with trauma, burn injury, sepsis and severe malnutrition. Replenishment of fibronectin levels has been correlated with clinical improvement in such patients.

Fibronectin has been found to have a molecular weight of 440,000 daltons and to consist of two nearly identical 220,000-dalton subunit polypeptides. Fibronectin compositions or concentrates can be made up of varying ratios of both the dimer (the 440,000-Dalton unit) and the monomer (the 220,000-dalton unit). It has been suggested that the activity of a fibronectin composition is relatively higher when the proportion of dimer to monomer is relatively higher.

Factor VIII, which is associated with the coagulation or clotting of blood, is present at deficient levels in certain individuals, or is absent. For example, persons who have a deficiency (or absence) of antihemophilic factor (AHF or Factor VIII), i.e., persons suffering from hemophilia A, have blood which either fails to clot or clots only after longer periods of time than the time required for clotting in a person who has a normal level of Factor VIII.

In the past, persons suffering from hemophilia A (hemophiliacs) were treated by transfusing them with whole blood or blood plasma. More recently, however, Factor VIII concentrates have become available for administration to such persons. Such Factor VIII concentrates are produced by fractionating blood plasma into various components and recovering the components separately, including the Factor VIII component. Some processes for producing Factor VIII concentrate have been based on a discovery by Poole et al (*Nature*, Vol. 203, p. 312, 1964) that the precipitate remaining after plasma is frozen and then thawed, i.e., the cryoprecipitate, contains Factor VIII in a concentrated form and excludes various other protein fractions. It was discovered that, in addition to Factor VIII, the cryoprecipitate also includes the major portion of the fibronectin component of plasma.

Work progressed over the years to perfect the separation of Factor VIII from other proteins in the cryoprecipitate, including the fibronectin component, so that the resulting products would incorporate increased concentrations of Factor VIII relative to the other proteins present in the plasma.

One area in which a substantial amount of work has been done in production of Factor VIII is based on the use of polyethylene glycol (PEG) to precipitate Factor VIII from other proteins in an aqueous cryoprecipitate solution. For example, U.S. Pat. No. 3,652,530, which issued on Mar. 28, 1972 to A. J. Johnson, discloses a process for preparing a Factor VIII concentrate by fractionating cryoprecipitate with PEG at a relatively lower concentration to precipitate fibrinogen and other proteins, and then increasing the PEG concentration to precipitate Factor VIII. There is no disclosure of the fate of the fibronectin.

U.S. Pat. No. Re. 29,698 to Fekete et al discloses a process for production of Factor VIII (AHF) by which heparin is added to a cryoprecipitate solution, along with PEG, to provide increased yields of precipitated Factor VIII. It is disclosed that the amount of heparin employed during the fractionation step can vary, with the optimum concentration being 1 unit of heparin per ml of the plasma solution, whereas concentrations of heparin greater than about 10 units per ml are to be avoided as dangerous.

It is desired to provide a process for producing fibronectin and Factor VIII which results in increased purity, higher concentration, and enhanced yields of both proteins. Further, it is desired that the process provide a fibronectin concentrate comprising a maximized ratio of fibronectin dimer to monomer.

SUMMARY OF THE INVENTION

A process is provided in accordance with this invention for producing fibronectin and Factor VIII concentrates of high purity, yield and concentration from blood plasma. The process includes the steps of obtaining a cryoprecipitate containing both fibronectin and Factor VIII from blood plasma and dissolving the cryoprecipitate in an aqueous solution containing heparin to provide a cryoprecipitate/heparin solution which contains from about 30 to about 150 units of heparin per milliliter of solution. The fibronectin and Factor VIII concentrates are then recovered from the cryoprecipitate/heparin solution.

In one embodiment of practice of the invention, PEG is added to the cryoprecipitate/heparin solution to provide a PEG concentration of from about 1% to about 5% to precipitate fibronectin, while leaving Factor VIII remaining in the solution. The fibronectin precipitate is recovered and further processed to provide the fibronectin concentrate, and the supernatant is processed to produce the Factor VIII concentrate.

BRIEF DESCRIPTION OF THE DRAWINGS

These and other features and advantages of the present invention will become better understood with reference to the following description, appended claims, and accompanying drawings, wherein:

DETAILED DESCRIPTION OF THE INVENTION

Figure 1:
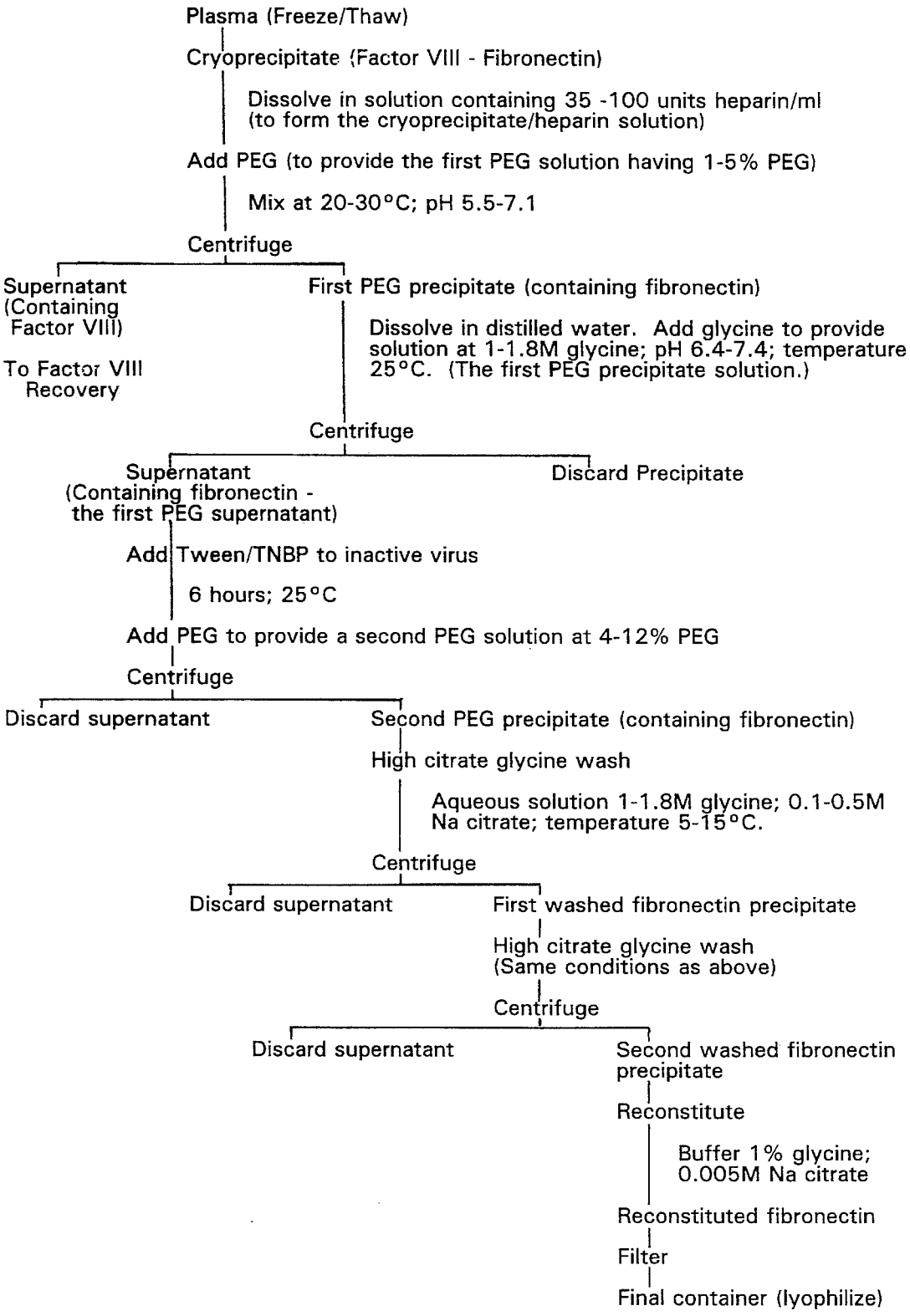
FIG. 1 is a flow chart illustrating an exemplary embodiment of a process provided in accordance with practice of the present invention for preparing a fibronectin concentrate from blood plasma.
Figure 2:
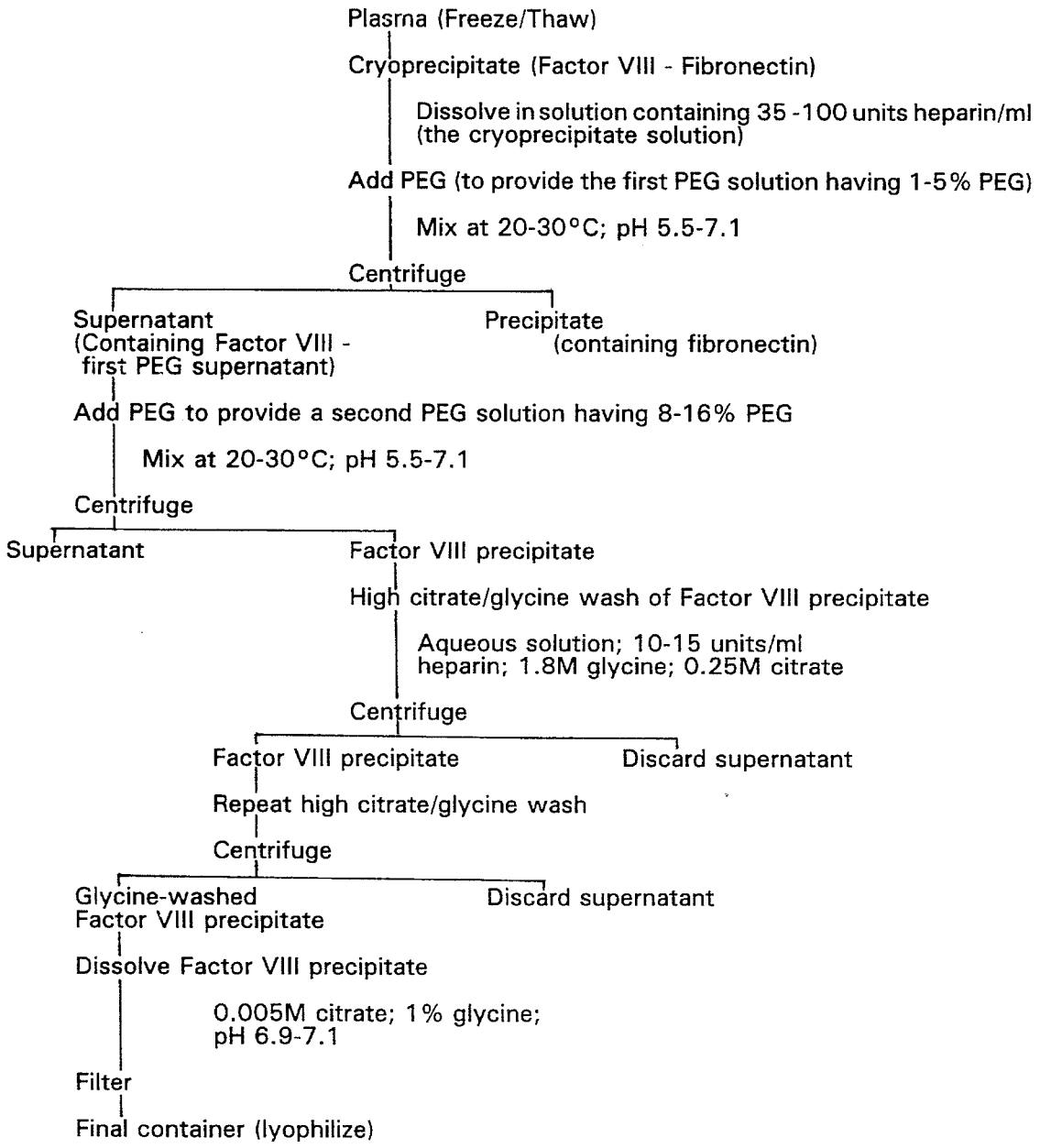
FIG. 2 is a flow chart illustrating an exemplary embodiment of a process provided in accordance with practice of the present invention for preparing a Factor VIII concentrate from blood plasma.

Preferred embodiments of the process provided in accordance with practice of principles of this invention for producing fibronectin and Factor VIII concentrates can be understood by referring to FIGS. 1 and 2, respectively, which are flow diagrams illustrating the process steps. As is described below in greater detail, both the fibronectin and Factor VIII are recovered from the same starting material, i.e., from cryoprecipitate. The process for the recovery of both begins with the steps of their separation from a cryoprecipitate solution.

Separation of the Fibronectin and Factor VIII Components of Cryoprecipitate

Turning first to FIG. 1, the process for preparing fibronectin is outlined, including the initial steps of separating the fibronectin from Factor VIII. Fibronectin and Factor VIII are initially separated from human blood plasma that has been collected and tested according to procedures approved by the U.S. Food and Drug Administration. The plasma is frozen at a temperature of about –20° C. and is subsequently thawed at 0° C. to 5° C. and pooled. During the thawing process, a precipitate forms (hereinafter called the "cryoprecipitate") which is removed by centrifugation and recovered for further purification and concentration.

The cryoprecipitate (which contains both the fibronectin and Factor VIII fractions of plasma) is dissolved in distilled water which contains from about 30 to about 150 units of heparin per milliliter (ml) of water. (The heparin-containing distilled water solution is hereinafter called the "heparin solution"). The heparin solution, which has been adjusted to a pH of from about 6.5 to about 7.5 with dilute hydrochloric acid (HCL) (or other appropriate acid such as acetic acid), is then mixed at a temperature of from about 20° C. to about 30° C. until the cryoprecipitate is completely dissolved to provide a cryoprecipitate/heparin solution. Preferably, the temperature during mixing is maintained at about 30° C., and the volume of heparin solution used is from about 2 to about 10 liters per kilogram of cryoprecipitate.

As used herein, one unit of heparin is defined to mean one U.S.P. (United States Pharmacopoeia) unit. The U.S.P. unit of heparin is that quantity which will prevent 1.0 ml of citrated sheep plasma from clotting for one hour after the addition of 0.2 ml of a 1:100 $CaCl_2$ solution. As used herein, the term "heparin" is meant to include heparin itself and the pharmaceutically-acceptable water soluble salts of heparin, e.g., the sodium salts. A suitable example of a commercially-available heparin sodium product is U.S.P. heparin from Lyphomed Company, of Melrose Park, Ill.

PEG powder, preferably having a molecular weight in the range of from about 2000 to about 6000 (more preferably, from about 3000 to 4000), is then added to the cryoprecipitate/heparin solution to provide a first PEG solution having a final PEG concentration of from about 1% to about 5% (wt/vol). The term (wt/vol) means the weight of material added per 100 ml of solution prior to the addition. The percentages used herein are all weight per volume unless otherwise indicated. Preferably, the PEG is added in the form of a solution prepared by dissolving the PEG in distilled water that contains a citrate (such as sodium citrate). In one exemplary embodiment, the aqueous PEG solution added to the cryoprecipitate/heparin solution contains about 31.5% PEG, 0.22% sodium citrate dihydrate and 0.08% citric acid monohydrate at a pH of 6.2.

The pH of the first PEG solution is adjusted to from about 5.5 to 7.1 with an acid such as dilute acetic acid. As is described later in detail, the yield and specific activity of Factor VIII is enhanced when the pH is from about 5.9 to 6.2 and, thus, it is preferred that the pH is adjusted to within this range and, most preferably, to about 6.1. The pH-adjusted first PEG solution is mixed for approximately 15 minutes, while being maintained at a temperature of from about 15° C. to about 35° C.

The addition of PEG (1%–5%) to form the first PEG solution results in precipitation of fibronectin, along with fibrinogen, leaving Factor VIII in the solution. The fibronectin and other precipitated proteins, i.e., the first PEG precipitate, are separated from the Factor VIII-containing solution by centrifugation. The first PEG precipitate is recovered and processed further to recover fibronectin, while the supernatant (the first PEG supernatant) is recovered and processed further to recover Factor VIII.

It has been found that the preferred mixing temperature of the first PEG solution is 20° C. to 30° C., with the temperature most preferred at 25° C. It was discovered that at temperatures less than about 25° C., and more particularly at temperatures less than about 20° C., Factor VIII precipitates with the fibronectin proteins to a greater degree than desired, thus reducing the yield of Factor VIII and reducing the specific activity of the fibronectin produced. At temperatures above about 25° C., and more particularly above about 30° C., increased bacterial growth and denaturation of protein occur.

While the range of the concentration of heparin in the cryoprecipitate/heparin solution can be from about 30 to about 150 units per ml, the preferred range is from about 40 to 100 units per ml and, most preferably, is about 80. At less than about 30 units per ml, an undesirably low amount of fibronectin is precipitated, while adding more than 150 units per ml does not sufficiently increase the amount of fibronectin precipitated to be economical. As is shown below in Example 4, about 80 units per ml of heparin is considered optimum.

While the range of from about 1% to about 5% PEG can be used in the first PEG solution, it is preferred that the solution have a PEG concentration of from about 3% to about 4% to maximize the precipitation of fibronectin. When the concentration of PEG in the solution is greater than about 5%, an undesirably large amount of Factor VIII is precipitated with the fibronectin proteins, and, thus, the specific activity of the final fibronectin product is reduced, as well as the yield of Factor VIII. If less than about 1% PEG is used, the amount of fibronectin proteins precipitated is less than desired. Thus, by adding PEG to a concentration of from about 1% to about 5%, the PEG concentration is high enough to precipitate fibronectin, but is below the concentration at which Factor VIII will precipitate.

Production of Fibronectin from First PEG Precipitate

The first PEG precipitate is dissolved in distilled water in an amount comprising from about 6 to about 20 times the total weight of the precipitate, to thereby form the first PEG precipitate solution. Glycine is added to the solution to a final concentration of from about 1 to about 1.8 moles per liter, i.e., from about 1 to about 1.8 molar (M) glycine. The pH of the solution is adjusted to between about 6.4 and about 7.4. In an exemplary embodiment, the pH is adjusted to 6.7. The temperature of the first PEG precipitate solution is maintained, preferably, between about 20° C. to about 30° C. In an exemplary embodiment, the temperature is maintained at 25° C. Various proteins, such as fibrinogen are precipitated from the first PEG precipitate solution by the addition of glycine. The solution is then centrifuged, the precipitate is discarded, and the supernatant (the first PEG supernatant), which contains fibronectin, is recovered.

PEG is added to the first PEG supernatant to a final PEG concentration of from about 4% to about 12% to provide a second PEG solution. As was the case for the PEG added to form the first PEG solution, when solid PEG is used, it is preferred that the PEG is added in the form of a solution containing citrate, e.g., sodium citrate, at a concentration of from about 0.01M to about 0.1M. Preferably, the concentration is about 0.05M sodium citrate. When PEG is added in solid form, the water volume used in dissolving the first PEG precipitate is preferably from about 10 to about 20 times the weight of the precipitate. The addition of PEG to the 4–12% concentration results in fibronectin precipitating from the solution during mixing. Such mixing is done for not less than about 30 minutes, at a temperature of from about 20° C. to about 30° C. The fibronectin precipitate is recovered from the second PEG solution by centrifugation.

The PEG added to form the second PEG solution preferably has a molecular weight in the range of from about 2000 to about 6000, more preferably in the range of from about 3000 to about 4000. Additionally, during the second PEG precipitation step, it is preferred that the mixing temperature be from about 20° C. to about 30° C., with the temperature most preferred at about 25° C.

Although the range of from about 4% to about 12% PEG in the second PEG solution is satisfactory, the range of about 8% to about 10% is preferred, with about 9% being most preferred. At less than about 8%, the amount of fibronectin precipitated is less than desired; at greater than about 12%, other proteins will precipitate, decreasing the specific activity of fibronectin.

The PEG-precipitated fibronectin, i.e., the second PEG precipitate, which is recovered by centrifugation, is preferably subjected to two identical citrate/glycine washes in succession. In an exemplary embodiment, the washes are accomplished by suspending the second PEG precipitate in a solution having a glycine concentration of from about 1M to about 1.8M and containing sodium citrate at a concentration of from about 0.1M to about 0.5M. The pH of the solution is preferably adjusted to 6.2 to 7.2 and is maintained at a temperature in the range of 5° C. to 25° C. After the suspension has been mixed thoroughly, e.g., by mixing for 30 minutes to 1 hour, it is centrifuged to recover the first glycine-washed fibronectin precipitate. The volume of the glycine solution is preferably from about 10 to about 30 liters per kilogram of the second PEG precipitate. The wash procedure is repeated to provide a second citrate/glycine wash and the second, or final, glycine-washed fibronectin precipitate is recovered, e.g., by centrifugation.

The citrate/glycine washes remove immunoglobulins, Beta globulins, and impurities from the fibronectin concentrate, as well as residual PEG. The citrate concentration preferred is from about 0.1M to 0.5M, with the most preferred range being from about 0.2M to 0.25M. It was found that if the citrate concentration used was less than about 0.1M, the immunoglobulins and Beta globulins were not removed as desired. If the citrate concentration is greater than about 0.5M, no further removal of impurities occurs. The pH of about 6.7 is optimum, with a range of 6.2 to 7.2 being satisfactory. If the temperature is greater than about 25° C., an undesirable amount of fibronectin will solubilize, thereby reducing the fibronectin yield.

After recovery, the glycine-washed fibronectin precipitate is reconstituted in an aqueous solution which, in one exemplary embodiment, includes 0.005M sodium citrate and 1% glycine. The reconstituted fibronectin solution is then filtered, placed into final containers, and lyophilized.

In preferred embodiments of practice of principles of this invention, the fibronectin production process includes steps for inactivating viruses that may be present in such blood products, e.g., hepatitis B virus, hepatitis non-A/non-B virus, HTLV III (AIDS virus), Cytomegalovirus, Epstein-Barr virus, and the like.

In one preferred embodiment of practice of the process of this invention, a solution comprising both an organic solvent and a detergent is added to the first PEG supernatant to inactivate virus that may be present. The amount of organic solvent and detergent added preferably results in a solution containing about 0.3% organic solvent and about 1% detergent. Detergents useful in practice of principles of the invention are a detergent sold under the trademark "TWEEN-80" by Fisher Scientific of Springfield, N.J., or a detergent sold under the trademark "TRITON X-100" by Aldrich Company of Milwaukee, Wis. Useful organic solvents are tri(n-butyl)phosphate (TNBP) and ethyl ether, and the like. The solution is incubated for about 6 hours, at a temperature of from about 24° C. to about 30° C.

After the organic solvent/detergent solution inactivates virus present in the protein being sterilized, the process is continued by adding PEG to the solution to thereby form the second PEG solution as described above, which results in precipitation of fibronectin. In other preferred embodiments, the organic solvent/detergent solution (the anti-viral solution) can be added at another stage of the process instead of to the first PEG supernatant. For example, the anti-viral solution can be added during either of the citrate glycine wash steps, or it can be added after the fibronectin is dissolved in the 0.005M citrate/1% glycine solution just prior to its being filled into the final containers. Inactivation of virus using organic solvent/detergent mixtures is disclosed in U.S. Pat. No. 4,540,573 which issued on Sep. 10, 1985 to Neurath et al. U.S. Pat. No. 4,540,573 is incorporated herein by this reference.

In a second preferred embodiment of practice of process of this invention, the steps applied to inactivate viruses can include heating, either alone or in combination with organic solvent/detergent inactivation. Such heat inactivation can, for example, include heating the fibronectin, after it is lyophilized, to at least about 60° C. for a period of time sufficient to inactivate the virus. The heating time can range from 10 hours to 100 hours, as appropriate, and the heating can be done with lyophilized fibronectin in bulk or in the final container.

One method that can be used in accordance with practice of the process of this invention for heating lyophilized fibronectin in bulk is to disperse (suspend) the lyophilized fibronectin in an organic liquid such as heptane. The fibronectin suspension is then heated at not less than about 60° C. for not less than about 10 hours, preferably not less than about 24 hours. After the heating step is concluded, the suspension is filtered, and the virus-inactivated fibronectin concentrate powder is recovered and air-dried to remove residual organic liquid. The air-dried, heat-treated fibronectin powder is then dissolved in a dextrose solution and filtered through previously-sterilized, bacteria-retentive membrane or cartridge filters, filled into the final container (a clean, sterilized vial), and lyophilized.

Various methods for heat treating lyophilized proteins to inactivate virus by suspending the proteins in organic liquids are disclosed in U.S. Pat. No. 4,490,361, which issued to C. Heldebrant on Dec. 25, 1984. U.S. Pat. No. 4,490,361 is incorporated herein by this reference.

The lyophilized fibronectin product produced in accordance with practice of this invention can be used for intravenous injection for treating trauma, burn injury, sepsis, or malnutrition after reconstitution in an appropriate amount of sterile water. In one example for treating severe malnutrition, the reconstituted fibronectin is administered to patients for 4 days at doses of from about 7 to about 21 mg of fibronectin per kg of body weight.

Various features and advantages of the process for producing fibronectin in accordance with practice of this invention are illustrated in the following examples. It is to be understood, however, that the examples merely illustrate the invention and are not intended to limit the scope of the invention, which is defined by the claims.

EXAMPLE 1

Preparation of Fibronectin Concentrate 410 grams of cryoprecipitate were dissolved in distilled water which contained about 80 units of heparin per milliliter at a pH of 7. The solution was mixed at a temperature of about 30° C. for about 30 minutes to provide a cryoprecipitate/heparin solution.

A PEG solution having a PEG concentration of 31.5%, 0.22% sodium citrate dihydrate, and 0.08% citric acid monohydrate at a pH of 6.2 was added to the cryoprecipitate/heparin solution to provide a PEG concentration of 3.5%. The resulting solution was mixed for 30 minutes at a temperature of 25° C. A precipitate was formed (the first PEG precipitate) which was separated from the solution by centrifugation. The first PEG precipitate was found to contain fibronectin, fibrinogen and immunoglobulins. The supernatant which contained Factor VIII was set aside.

155 grams of the first PEG precipitate were dissolved in distilled water in an amount which comprised about 8 times the total weight of the precipitate to form the first PEG precipitate solution. Glycine was added to the solution to a final concentration of 1.7M, and the pH of the solution was adjusted to about 6.6. The temperature of the solution was maintained at about 25° C., and the solution was centrifuged, and the supernatant, which contained fibronectin, was recovered.

The PEG solution was added to 1260 ml of the supernatant to provide a solution with a PEG concentration of about 9% (the second PEG solution). The second PEG solution was mixed for approximately 30 minutes at a temperature of about 25° C., during which time a precipitate formed (the second PEG precipitate). The solution was centrifuged, and the precipitate was recovered.

The second PEG precipitate was then subjected to two identical citrate/glycine washes in succession. 48 grams of the second PEG precipitate were suspended in a solution having a glycine concentration of about 1.8M and containing sodium citrate at a concentration of about 0.25M. The pH of the solution was adjusted to 6.7 and maintained at a temperature of 20° C. After the suspension was mixed thoroughly by mixing for 30 minutes, it was centrifuged to recover the first glycine-washed fibronectin precipitate. The citrate wash procedure was then repeated.

The glycine-washed fibronectin precipitate was reconstituted in an aqueous solution of 0.005M sodium citrate and 1% glycine to provide a final bulk solution. The solution was then filtered, placed into final containers, and lyophilized.

It was found that the final fibronectin product was 100% pure by a cellulose acetate electrophoresis process, i.e., it was devoid of fibrinogen and immunoglobulin impurities.

EXAMPLE 2

Monkey Kidney Cell Adhesion to Fibronectin

A portion of a fibronectin sample prepared according to the process of Example 1 was tested for biological functional cell attachment assay. The fibronectin sample supported the MK2 (Rhesus monkey kidney) cell attachment on microtiter wells at very low concentrations (0.3 micrograms fibronectin/ml).

EXAMPLE 3

Characterization of Fibronectin by the Process of This Invention

A portion of a fibronectin sample prepared according to the process of Example 1 was analyzed for molecular weight protein patterns under reduced and non-reduced conditions using 5% sodium dodecyl sulfate (SDS) electrophoresis in conjunction with immunoblotting analysis (Western blotting). (The procedures for the SDS and Western blotting analysis are outlined in Blumenstock, F. et al, "Progressive Loss of Fibronectin - Mediated Opsonic Activity in Plasma Cryoprecipitate with Storage," Vox Sang, 54, pp. 129–137 (1988).)

The fibronectin sample shows greater than 90% fibronectin dimer (supported by protein staining and immunoblotting analysis) and is devoid of low molecular weight protein impurities. A complete conversion of fibronectin dimer into fibronectin monomer subunits occurs upon reduction by 10 mM beta-mercaptoethanol.

Having a fibronectin product of high purity which is non-degraded and non-fragmented, and thus which has a relatively high dimer content, i.e., greater than 90% dimer, may provide enhanced in vivo activity and response.

EXAMPLE 4

Effect of Varying Concentrations of Heparin on the Separation of Fibronectin from Cryoprecipitate 250 grams of cryoprecipitate were divided into five 50-gram portions. Each 50-gram portion was dissolved at 30° C. in 150 grams of water containing various amounts of heparin. The concentration of heparin in the five solutions was 0, 13, 53, 80 and 133 units of heparin per milliliter of solution (u/ml).

The pH of each of the five solutions was adjusted to approximately 7, using 0.1 normal (N) hydrochloric acid (HCl). A PEG solution containing 0.01M sodium citrate and 0.004M citric acid was added to each solution at 25° C. to provide a final PEG concentration of approximately 3.5%. The pH of each solution was adjusted to about 6.1, using 1 N acetic acid.

The suspensions were centrifuged at 25° C., and the precipitates were collected and each was dissolved in distilled water using a ratio of 1 gram of precipitate to 6 grams of distilled water. The pH of each solution was adjusted to 6.8 by the addition of 1N acetic acid, and glycine was added to each solution at 20° C. to provide solutions having a 1.8M glycine concentration. The suspensions were then centrifuged, and the supernatants collected. The supernatants were assayed for fibronectin content by cellulose acetate electrophoresis and RID (radial immuno diffusion) methods.

Table 1 below sets forth the results of the fibronectin assays of each of the five solutions, in units of milligrams of fibronectin per liter of plasma (mg/L).

TABLE 1

| Soln. No. | Heparin (in cryo solution) | Fibronectin mg/L (by electrophoresis) | Fibronectin mg/L (by RID) |
|---|---|---|---|
| 1 | 0 u/ml | 37 | 55 |
| 2 | 13 | 50 | 62 |
| 3 | 53 | 75 | 69 |
| 4 | 80 | 81 | 82 |
| 5 | 133 | 86 | 89 |

As can be seen by the results of the experiments of Example 4, the amount of fibronectin precipitated from solution increased as the amount of heparin in the solution increased. For example, the amount of fibronectin precipitated when 80 u/ml of heparin are used, based on the RID analysis, is 132% of the amount of fibronectin precipitated when only 13 u/ml heparin are used. The difference is even greater when the data from the electrophoresis method is correlated.

Production of Factor VIII from the First PEG Supernatant

The recovery of Factor VIII from the first PEG supernatant provided in accordance with the process described above is accomplished by first adding PEG to the first PEG supernatant to provide a second PEG solution with a PEG concentration of from about 8% to about 16%. As was the case for the PEG added to form the first PEG solution, it is preferred that the PEG is added in the form of a solution containing citrate, e.g., sodium citrate, at a concentration of from about 0.01M to about 0.1M. The addition of PEG to the 8–16% concentration results in Factor VIII precipitating from the second PEG solution during mixing, which is continued for not less than about 15 minutes at a temperature of from 20° C. to 30° C. In an exemplary embodiment, the Factor VIII precipitate is recovered from the second PEG solution by centrifugation.

The PEG added to form the second PEG solution preferably has a molecular weight in the range of from about 2000 to about 6000, more preferably in the range of from about 3000 to about 4000. Additionally, during precipitation of Factor VIII from the second PEG solution, it is preferred that the mixing temperature be from about 15° C. to about 30° C., with the temperature most preferred at about 25° C. It was discovered that at temperatures less than about 15° C., and more particularly at temperatures less than about 10° C., protein impurities will precipitate along with Factor VIII, thereby reducing the specific activity of the Factor VIII in the final product.

Although the range of from about 8% to about 16% in the second PEG solution is satisfactory, the range of about 9% to about 15% is preferred, with about 12% being most preferred. At less than about 8%, the precipitated Factor VIII yield is less than desired; at greater than about 16%, unwanted proteins will precipitate with Factor VIII, thereby reducing the specific activity of Factor VIII in the final product.

The Factor VIII precipitated from the second PEG solution is preferably subjected to two identical citrate/glycine washes in succession. In an exemplary embodiment, the washes are accomplished by suspending the PEG-precipitated Factor VIII in a 1M to 2M glycine solution, which includes from about 10 to about 20 units of heparin per ml of solution, about 0.25M citrate, has a pH of about 6.7, and is maintained at a temperature in the range of 0° C. to 15° C. If desired, heparin can be omitted. It is preferred, however, that heparin is used to provide enhanced stability to the Factor VIII if a viral inactivation step comprising heat is performed subsequent to the wash steps. After the suspension has been mixed thoroughly, e.g., by mixing for about 30 to about 60 minutes, it is centrifuged to recover the glycine-washed Factor VIII precipitate. The volume of the glycine solution is preferably from about 5 to about 35 liters per kilogram of PEG-precipitated Factor VIII. The wash procedure is repeated to provide a second citrate/glycine wash and the final glycine-washed Factor VIII precipitate is recovered, e.g., by centrifugation.

The citrate/glycine washes remove immunoglobulins and Beta globulins from the Factor VIII concentrate, as well as residual PEG. The citrate concentration preferred is from about 0.1M to 0.5M, with the most preferred range being from about 0.2M to 0.25M. It was found that if the citrate concentration used was less than about 0.1M, the immunoglobulins and Beta globulins were not removed as desired. If the citrate concentration is greater than about 0.5M, no further benefit is observed. The pH of 6.7 is optimum, with a range of 6.2 to 7.2 being satisfactory. Preferably, the washes are done at less than 15° C. to minimize the amount of Factor VIII dissolved in the wash solution.

After recovery, the glycine-washed Factor VIII precipitate is reconstituted in an aqueous solution which, in one exemplary embodiment, includes 0.005M citrate and 1% glycine. The solution is then filtered, placed into final containers, and lyophilized.

In preferred embodiments of practice of principles of this invention, the process includes steps for inactivating viruses that may be present in the blood products, as was described above for the fibronectin process. In one preferred embodiment of practice of the process of this invention, a solution comprising an organic solvent and a detergent is added to the first PEG supernatant to inactivate virus that may be present. The amounts and types of organic solvents and detergents are the same as those described above for viral inactivation in the fibronectin process.

After the organic solvent/detergent solution inactivates virus present in the protein being sterilized, the process is continued as set forth above by adding PEG to thereby form the second PEG solution to precipitate Factor VIII. In other preferred embodiments, the organic solvent/detergent solution (the anti-viral solution) can be added at another stage of the process instead of to the first PEG supernatant. For example, the anti-viral solution can be added during the citrate glycine wash, or it can be added after the Factor VIII is dissolved in the 0.005M citrate/1% glycine solution just prior to its being filled into the final containers.

As was described above with regard to fibronectin, in a second preferred embodiment of practice of process of this invention to produce Factor VIII, the steps applied to inactivate viruses can include heating, either alone or in combination with organic solvent/detergent inactivation. The procedures used for Factor VIII are the same as those described above for fibronectin. Thus, one method that can be used for heating lyophilized Factor VIII in bulk, is to disperse (suspend) the lyophilized Factor VIII in an organic liquid such as heptane. The Factor VIII suspension is then heated at not less than about 60° C. for not less than about 10 hours, preferably not less than about 24 hours. After the heating step is concluded, the suspension is filtered, and the virus-inactivated Factor VIII concentrate powder is recovered and air-dried to remove residual organic liquid. The air-dried, heat-treated Factor VIII powder is then dissolved in a dextrose solution and filtered through previously-sterilized, bacteria-retentive membrane or cartridge filters, filled into the final container (a clean, sterilized vial), and lyophilized.

The lyophilized Factor VIII product produced in accordance with practice of this invention can be used for intravenous injection to treat hemophilia after reconstitution in an appropriate amount of sterile water.

Examples of processes provided in accordance with this invention for production of Factor VIII are set forth below.

EXAMPLE 5

Human plasma (Type O) was initially frozen at a temperature of about −20° C. The frozen plasma was then thawed at from 0° C. to 5° C. and pooled. The cryoprecipitate which formed during the thawing process was then removed by centrifugation and recovered.

100 grams of cryoprecipitate was dissolved in 300 ml of distilled water, and liquid U.S.P. heparin from Lyphomed Company was added to provide a cryoprecipitate/heparin solution containing 2.7 units of heparin per ml of solution. The solution was adjusted to a pH of 7 with 0.1N HCl and was then mixed at 30° C. for 30 minutes.

Solid PEG powder, having a molecular weight of 3500 was provided in a solution containing about 0.05M sodium citrate. A portion of the PEG solution was added to the cryoprecipitate/heparin solution to provide a first PEG solution with a final PEG concentration of 3.5%. The first PEG solution was thoroughly mixed at 25° C. for 15 minutes. The pH of the solution was adjusted to 6.3, with dilute acetic acid, and the solution was then mixed at about 25° C. for about 30 minutes to precipitate unwanted proteins from the Factor VIII. The precipitate was removed by centrifugation and saved for further processing into a fibronectin concentrate. The supernatant (the first PEG supernatant), which contained the Factor VIII, was retained for further processing into a second portion of the Factor VIII concentrate.

The PEG solution was added to the first PEG supernatant to bring the concentration of PEG to 12%. The increased concentration of PEG resulted in precipitation of Factor VIII, and the suspension containing the Factor VIII precipitate was mixed for 15 minutes at 25° C. The Factor VIII precipitate was recovered by centrifugation and subjected to two identical glycine/citrate washes in succession. The supernatant was discarded. The glycine/citrate washes included suspending the Factor VIII precipitate in a 1.8M glycine solution containing 14 units of heparin per ml of solution, 0.25M sodium citrate, and a pH of about 6.7. The temperature of the suspension was maintained at 5° C. during mixing, which took approximately 30 minutes. The suspension was then centrifuged and the Factor VIII precipitate recovered. The glycine/citrate wash procedure was repeated.

The glycine-washed Factor VIII precipitate was recovered by centrifugation and was reconstituted in an aqueous solution of 0.005M citrate and 1% glycine at a pH of 7.25 to provide the final bulk solution.

The yield of Factor VIII activity in the final bulk was measured by APTT one-stage assay and found to be 170 units (Factor VIII activity) per kilogram of plasma, with a final bulk yield of 54%. (The procedure for the APTT one-stage assay is outlined in Langdell, R. et al, *Journal of Lab. Clin. Med.*, Vol. 41, pp. 637–647 (1953).) The final bulk yield is defined as the total Factor VIII activity in the final bulk divided by the total Factor VIII activity in the cryoprecipitate. The specific activity of the Factor VIII product was found to be 5.6 units of Factor VIII activity per mg of protein recovered.

EXAMPLE 6

The procedure of Example 5 was repeated except that sufficient heparin was added to the cryoprecipitate solution to provide a cryoprecipitate/heparin solution which contained 67 units of heparin per ml of solution.

The yield of Factor VIII activity in the final bulk was measured and found to be 180 units per kilogram of plasma, with a final bulk yield of 53%. The specific activity of the Factor VIII product was found to be 6.4 units of Factor VIII activity per mg of protein recovered.

EXAMPLE 7

The procedure of Example 5 was repeated except that sufficient heparin was added to the cryoprecipitate solution to provide a cryoprecipitate/heparin solution which contained 73 units of heparin per ml of solution.

The yield of Factor VIII activity in the final bulk was measured and found to be 272 units per kilogram of plasma, with a final bulk yield of 65%. The specific activity of the Factor VIII product was found to be 8.9 units of Factor VIII activity per mg of protein recovered.

EXAMPLE 8

The procedure of Example 5 was repeated except that sufficient heparin was added to the cryoprecipitate solution to provide a cryoprecipitate/heparin solution which contained 80 units of heparin per ml of solution.

The yield of Factor VIII activity in the final bulk was measured and found to be 251 units per kilogram of plasma, with a final bulk yield of 63%. The specific activity of the Factor VIII product was found to be 12.7 units of Factor VIII activity per mg of protein recovered.

EXAMPLE 9

The procedure of Example 8 was repeated. The yield of Factor VIII activity in the final bulk was measured and found to be 217 units per kilogram of plasma, with a final bulk yield of 69%. The specific activity of the Factor VIII product was found to be 13.9 units of Factor VIII activity per mg of protein recovered.

EXAMPLE 10

A control was run using the same procedure as Example 5 except that no heparin was added to the distilled water in which the cryoprecipitate was dissolved.

The yield of Factor VIII activity in the final bulk was measured and found to be 199 units per kilogram of plasma, with a final bulk yield of 65%. The specific activity of the Factor VIII product was found to be 5.6 units of Factor VIII activity per mg of protein recovered.

Table 2 lists the results of a Examples 5 through 10.

TABLE 2

| Example | Units/ml Heparin In Solution | Final Bulk Yield (Units Factor VIII Activity/kg Total Recovered Precipitate) | Factor VIII Yield at Final Bulk* | Specific Activity (Units Factor VIII Activity/mg Total Protein) |
|---|---|---|---|---|
| 5 | 2.7 | 170 | 54% | 5.6 |
| 6 | 67.0 | 180 | 53% | 6.4 |
| 7 | 73.0 | 272 | 65% | 8.9 |
| 8 | 80.0 | 251 | 63% | 12.7 |
| 9 | 80.0 | 217 | 69% | 13.9 |
| 10 | (0) | 199 | 65% | 5.6 |

*Final Bulk Yield = Units of Factor VIII in final bulk per units of Factor VIII in cryoprecipitate.

As is shown in Examples 5–10, the specific activity of the Factor VIII concentrate was unexpectedly significantly increased when greater than about 80 units of heparin was used per ml of the cryoprecipitate solution. The specific activity was the same for the control (Example 10) where no heparin was used and for Example 5 where 2.7 units of heparin per ml were used.

Examples 11–13 were conducted using the same procedure as Example 5 except that Type A plasma was used.

EXAMPLE 11

The procedure of Example 5 was repeated except that Type A plasma was used instead of Type O, and sufficient heparin was added to the cryoprecipitate solution to provide a cryoprecipitate/heparin solution which contained 1.7 units of heparin per ml of solution.

The yield of Factor VIII activity in the final bulk was measured and found to be 186 units per kilogram of plasma, with a final bulk yield of 34%. The specific activity of the Factor VIII product was found to be 6.7 units of Factor VIII activity per mg of protein recovered.

EXAMPLE 12

The procedure of Example 11 was repeated except that the cryoprecipitate/heparin solution contained 80 units of heparin per ml of solution.

The yield of Factor VIII activity in the final bulk was measured and found to be 306 units per kilogram of plasma, with a final bulk yield of 66%. The specific activity of the Factor VIII product was found to be 11.4 units of Factor VIII activity per mg of protein recovered.

EXAMPLE 13

The procedure of Example 12 was repeated. The yield of Factor VIII activity in the final bulk was measured and found to be 261 units per kilogram of plasma, with a final bulk yield of 47%. The specific activity of the Factor VIII product was found to be 13.2 units of Factor VIII activity per mg of protein recovered.

EXAMPLE 14

The procedure of Example 11 was repeated except that the cryoprecipitate/heparin solution contained 273 units of heparin per ml of solution.

The yield of Factor VIII activity in the final bulk was measured and found to be 156 units per kilogram of plasma, with a final bulk yield of 38%. The specific activity of the Factor VIII product was found to be 5.2 units of Factor VIII activity per mg of protein recovered.

Table 3 lists the results of Example 11–14.

TABLE 3

| Example | Units/ml Heparin In Solution | Final Bulk Yield (Units Factor VIII Activity/kg Total Recovered Precipitate) | Factor VIII Yield at Final Bulk | Specific Activity (Units Factor VIII Activity/mg Total Protein) |
|---|---|---|---|---|
| 11 | 1.7 | 186 | 34% | 6.7 |
| 12 | 80.0 | 306 | 66% | 11.4 |
| 13 | 80.0 | 261 | 47% | 13.2 |
| 14 | 273.0 | 156 | 38% | 5.2 |

Examples 15 and 16 were conducted using the same procedure as Example 5 except that Type B plasma was used.

EXAMPLE 15

The procedure of Example 5 was repeated except that Type B plasma was substituted for Type O plasma, and the cryoprecipitate/heparin solution contained 1.7 units of heparin per ml of solution.

The yield of Factor VIII activity in the final bulk was measured and found to be 312 units per kilogram of plasma, with a final bulk yield of 54%. The specific activity of the Factor VIII product was found to be 6.3 units of Factor VIII activity per mg of protein recovered.

EXAMPLE 16

The procedure of Example 15 was repeated except that the heparin solution contained 80 units of heparin per ml.

The yield of Factor VIII activity in the final bulk was measured and found to be 349 units per kilogram of plasma, with a final bulk yield of 61%. The specific activity of the Factor VIII product was found to be 12.7 units of Factor VIII activity per mg of protein recovered.

Table 4 lists the results of Examples 15 and 16.

TABLE 4

| Example | Units/ml Heparin In Solution | Final Bulk Yield (Units Factor VIII Activity/kg Total Recovered Precipitate) | Factor VIII Yield at Final Bulk | Specific Activity (Units Factor VIII Activity/mg Total Protein) |
|---|---|---|---|---|
| 15 | 1.7 | 312 | 54% | 5.3 |
| 16 | 80.0 | 349 | 61% | 12.7 |

Examples 17–22 were conducted to show the effect of pH on both the final bulk yield and specific activity of the Factor VIII product.

EXAMPLE 17

The procedure of Example 5 was repeated except that the cryoprecipitate solution contained 80 units of heparin per ml, and the pH of the first PEG solution was adjusted to 5.5 with dilute 1M acetic acid.

The yield of Factor VIII activity in the final bulk was measured and found to be approximately 30 units per kilogram of plasma, and the specific activity of the Factor VIII product was found to be about 2 units of Factor VIII activity per mg of protein recovered.

EXAMPLE 18

The procedure of Example 17 was repeated except that the pH of the first PEG solution was adjusted to 5.75.

The yield of Factor VIII activity in the final bulk was measured and found to be approximately 145 units per kilogram of plasma, and the specific activity of the Factor VIII product was found to be about 13 units of Factor VIII activity per mg of protein recovered.

EXAMPLE 19

The procedure of Example 17 was repeated except that the pH of the first PEG solution was adjusted to 6.0.

The yield of Factor VIII activity in the final bulk was measured and found to be approximately 200 units per kilogram of plasma, and the specific activity of the Factor VIII product was found to be about 20 units of Factor VIII activity per mg of protein recovered.

EXAMPLE 20

The procedure of Example 17 was repeated except that the pH of the first PEG solution was adjusted to 6.1.

The yield of Factor VIII activity in the final bulk was measured and found to be approximately 248 units per kilogram of plasma, and the specific activity of the Factor VIII product was found to be about 27 units of Factor VIII activity per mg of protein recovered.

EXAMPLE 21

The procedure of Example 17 was repeated except that the pH of the first PEG solution was adjusted to 6.15.

The yield of Factor VIII activity in the final bulk was measured and found to be approximately 220 units per kilogram of plasma, and the specific activity of the Factor VIII product was found to be about 11 units of Factor VIII activity per mg of protein recovered.

EXAMPLE 22

The procedure of Example 17 was repeated except that the pH of the first PEG solution as adjusted to 6.35.

The yield of Factor VIII activity in the final bulk was measured and found to be approximately 220 units per kilogram of plasma, and the specific activity of the Factor VIII product was found to be about 7 units of Factor VIII activity per mg of protein recovered.

Table 5 lists the results of Example 17–22.

TABLE 5

| Example | Units/ml Heparin In Solution | pH | Final Bulk Yield (Units Factor VIII Activity/kg Plasma) | Specific Activity (Units Factor VIII Activity/mg Total Protein) |
|---|---|---|---|---|
| 17 | 80 | 5.50 | 30 | 2.0 |

TABLE 5-continued

| Example | Units/ml Heparin In Solution | pH | Final Bulk Yield (Units Factor VIII Activity/kg Plasma) | Specific Activity (Units Factor VIII Activity/mg Total Protein) |
|---|---|---|---|---|
| 18 | 80 | 5.75 | 145 | 13.0 |
| 19 | 80 | 6.00 | 200 | 20.0 |
| 20 | 80 | 6.10 | 248 | 27.0 |
| 21 | 80 | 6.15 | 220 | 11.0 |
| 22 | 80 | 6.35 | 220 | 7.0 |

It can be seen that the yield and specific activity of the final Factor VIII product is increased when the pH of the first PEG solution is between about 6.0 to about 6.2. Preferably, the pH is about 6.1.

EXAMPLE 23

The procedure of Example 5 was repeated except that the cryoprecipitate solution contained 80 units of heparin per ml of solution, and the liquid used to provide both the 3.5% and 12% PEG solutions contained 0.011M citrate.

The percent yield of Factor VIII in the final bulk was measured at 62% with a specific activity of 5 units per mg of protein.

EXAMPLE 24

The procedure of Example 23 was repeated except that the PEG solution was added without citrate.

The percent yield of Factor VIII in the final bulk was measured at 38%, and the specific activity was 3.8 units of Factor VIII activity per mg of protein.

As can be seen from Examples 23 and 24, having citrate present in the liquid PEG solution increases both the percent final bulk yield and specific activity of Factor VIII in the final product.

The Examples 25 through 32 compare the yield of the final Factor VIII product when using different pH and PEG concentrations in the first PEG solutions but maintaining both the first and second PEG solutions at 25° C.

EXAMPLE 25

The procedure of Example 5 was repeated except that the PEG concentration in the first PEG solution was 3.3%, and the pH of the solution was adjusted to 6.5. The specific activity of the Factor VIII produced was 3.9, and the final bulk yield was 50%.

EXAMPLE 26

The procedure of Example 5 was repeated except that the PEG concentration in the first PEG solution was 3.5%, and the pH of the solution was adjusted to 6.5. The specific activity of the Factor VIII produced was 5, and the final bulk yield was 50%.

EXAMPLE 27

The procedure of Example 5 was repeated except that the PEG concentration in the first PEG solution was 3.5%, and the pH of the solution was adjusted to 6.35. The specific activity of the Factor VIII produced was 12, and the final bulk yield was 65%.

EXAMPLE 28

The procedure of Example 5 was repeated except that the PEG concentration in the first PEG solution was 3.6%, and the pH of the solution was adjusted to 6.5. The specific activity of the Factor VIII produced was 5.9, and the final bulk yield was 50%.

EXAMPLE 29

The procedure of Example 5 was repeated except that the PEG concentration in the first PEG solution was 3.6%, and the pH of the solution was adjusted to 6.6. The specific activity of the Factor VIII produced was 4.4, and the final bulk yield was 45%.

EXAMPLE 30

The procedure of Example 5 was repeated except that the PEG concentration in the first PEG solution was 3.8%, and the pH of the solution was adjusted to 6.35. The specific activity of the Factor VIII produced was 11.5, and the final bulk yield was 26%.

EXAMPLE 31

The procedure of Example 5 was repeated except that the PEG concentration in the first PEG solution was 4%, and the pH of the solution was adjusted to 6.8. The specific activity of the Factor VIII produced was 1.9, and the final bulk yield was 40%.

Table 6 lists the results of Example 25–31.

TABLE 6

| Example | % PEG In First PEG Solution | pH | Specific Activity (Units of Factor VIII Activity Per Mg of Total Protein) | Bulk Yield % |
|---|---|---|---|---|
| 25 | 3.3 | 6.5 | 3.9 | 50 |
| 26 | 3.5 | 6.5 | 5.0 | 50 |
| 27 | 3.5 | 6.35 | 12.0 | 65 |
| 28 | 3.6 | 6.5 | 5.9 | 50 |
| 29 | 3.6 | 6.6 | 4.4 | 45 |
| 30 | 3.8 | 6.35 | 11.5 | 26 |
| 31 | 4.0 | 6.8 | 1.9 | 40 |

It can be seen that the optimum conditions for recovery and specific activity of Factor VIII from a PEG solution processed at 25° C. appear to be achieved when the PEG concentration is approximately 3.5%.

EXAMPLE 32

Comparison of the Amount of Factor VIII Precipitated from Cryoprecipitate When Using Heparin Alone Versus Using Heparin Plus PEG for Such Precipitation Three 100-gram samples of cryoprecipitate were obtained. In the process where heparin alone was used to precipitate proteins from the solution, one of the 100-gram samples of cryoprecipitate was dissolved in 20 mM tris (3:1) buffer solution, and 80 u/ml of heparin was added at 25° C. and at a pH of approximately 6.8. The resulting suspension was centrifuged at 25° C., and the Factor VIII present in the supernatant was concentrated into a precipitate by adding PEG to a final concentration of 12%. The Factor VIII precipitate was dissolved in a 0.01M sodium citrate solution, using a ratio of 20 grams of water per gram of precipitate, and the solution was filtered. Assays were conducted on the solution to determine the amount of fibrinogen, total protein, and the Factor VIII yield.

In the process where both heparin and PEG were used to precipitate proteins from the solution, the second 100-gram sample of cryoprecipitate was dissolved in a heparin solution containing 80 units of heparin per ml of solution at a pH of approximately 7. PEG was added to the solution to bring the PEG concentration of the solution to 3.5%. The resulting suspension was centrifuged at 25° C., and the Factor VIII present in the supernatant was concentrated into a precipitate by adding PEG to a final concentration of 12%. The Factor VIII precipitate was dissolved in a 0.01M sodium citrate solution, using a ratio of 20 grams of water per gram of precipitate, and the solution was filtered. Assays were conducted on the solution to determine the amount of fibrinogen, total protein, and Factor VIII yield.

The third 100-gram sample was dissolved in 20 mM tris buffer solution and was assayed for fibrinogen, total protein and Factor VIII yield.

The assays were conducted using cellulose acetate electrophoresis, and total protein concentration was determined at 280 nanometers.

Table 7 shows the concentrations of fibrinogen in mg per ml of solution, total protein in mg per ml of solution, and Factor VIII yield in units/kg of plasma.

TABLE 7

| | Total Fibrinogen Remaining In Solution (mg/ml) | Total Protein Remaining In Solution (mg/ml) | Units of Factor VIII Remaining In Solution (Per kg of Plasma |
|---|---|---|---|
| Reconstituted cryoprecipitate | 14.6 mg/ml | 24.0 mg/ml | 372 u/kg |
| After heparin precipitation: | 8.1 mg/ml | 13.7 mg/ml | 196 u/kg |
| After heparin plus PEG precipitation: | 2.0 mg/ml | 8.9 mg/ml | 213 u/kg |

It can be seen from the results shown in Table 7 that using PEG in combination with heparin is much more effective in precipitating the fibrinogen and other impurities from the Factor VIII than using heparin alone for the separation.

The above descriptions of exemplary embodiments of processes for producing fibronectin and Factor VIII concentrates are for illustrative purposes. Because of variations which will be apparent to those skilled in the art, the present invention is not intended to be limited to the particular embodiments described above. The scope of the invention is defined in the following claims.

What is claimed is:

1. A process for producing a Factor VIII concentrate from blood plasma, the process comprising the steps of:

(a) obtaining a cryoprecipitate containing Factor VIII from blood plasma;

(b) dissolving the cryoprecipitate in an aqueous solution containing heparin in an amount sufficient to provide a cryoprecipitate/heparin solution containing from about 30 to about 150 units of heparin per milliliter of solution:

(c) adding a sufficient amount of a precipitant consisting essentially of PEG to the cryoprecipitate/heparin solution while maintaining the solution at a temperature of from 20° C. to 30° C. to precipitate protein contaminants, leaving a PEG supernatant containing Factor VIII;

(d) recovering the PEG supernatant; and (e) recovering Factor VIII from the PEG supernatant.

2. The process of claim 1 wherein the cryoprecipitate/heparin solution contains from about 35 to about 100 units of heparin per milliliter of solution.

3. The process of claim 1 wherein the pH of the solution of step (c) is adjusted to from about 5.9 to about 6.2.

4. The process of claim 1 additionally comprising the steps of:

(a) adding PEG to the PEG supernatant to provide a PEG concentration of from about 8% to about 16% to precipitate Factor VIII;

(b) recovering and then washing the Factor VIII precipitate in an aqueous solution having a glycine concentration of from about 0.1M to about 2.6M, a citrate concentration of from about 0M to about 0.5M and containing from about 10 to about 15 units per milliliter of heparin; and (c) recovering the washed Factor VIII precipitate by centrifugation.

5. A Factor VIII concentrate produced by the process of claim 1.

6. The process of claim 1, wherein the cryoprecipitate/heparin solution contains from at least about 80 to about 150 units of heparin per milliliter of solution and the pH of the solution is adjusted to about 6.3.

7. A process for producing a Factor VIII concentrate from blood plasma, the process comprising the steps of:

(a) obtaining a cryoprecipitate containing Factor VIII from the blood plasma;

(b) dissolving the cryoprecipitate in an aqueous solution containing heparin in an amount sufficient to provide a cryoprecipitate/heparin solution containing from about 30 to about 150 units of heparin per milliliter of solution;

(c) adding a precipitant consisting essentially of PEG to the cryoprecipitate/heparin solution, while maintaining the solution at a temperature of from 20° C. to 30° C., to provide a first solution having a PEG concentration of from about 1% to about 5% and adjusting the pH of the solution to from about 5.9 to about 6.2 to thereby precipitate unwanted protein contaminants from the solution to provide a first PEG supernatant containing Factor VIII;

(d) recovering the first PEG supernatant;

(e) adding an additional precipitant consisting essentially of PEG to the first PEG supernatant to bring the PEG concentration to from about 8% to about 16%, while maintaining the solution at a temperature of from about 15° C. to about 30° C., to thereby precipitate Factor VIII from the supernatant;

(f) recovering and then washing the Factor VIII precipitate in an aqueous solution containing (1) glycine at a concentration of from about 1.0M to about 2.6M, (2) citrate, and (3) heparin at a concentration of from about 10 to about 15 units heparin per milliliter of solution, wherein the wash is maintained at less than about 15° C.; and (g) recovering the washed Factor VIII precipitate.

8. The process of claim 7 wherein during step (c) the first PEG solution is maintained at a temperature of about 25° C. during precipitation of unwanted protein contaminated.

9. The process of claim 7 wherein during step (c) the pH of the first PEG solution is adjusted to about 6.1.

10. A factor VIII concentrate produced by the process of claim 7.

11. The process of claim 7, wherein the cryoprecipitate/heparin solution contains from at least about 80 to about 150 units of heparin per milliliter of solution and the pH of the solution is adjusted to about 6.3.

12. A process for producing a Factor VIII concentrate from blood plasma, the process comprising the steps of:

(a) obtaining a cryoprecipitate containing Factor VIII from blood plasma;

(b) dissolving the cryoprecipitate in an aqueous solution containing heparin in an amount sufficient to provide a cryoprecipitate/heparin solution containing from about 30 to about 150 units of heparin per milliliter of solution;

(c) adding a precipitant consisting essentially of PEG to the cryoprecipitate/heparin solution to provide a first solution having a PEG concentration of from about 1% to about 5% and adjusting the pH of the solution to from about 5.9 to about 6.2 to thereby precipitate unwanted protein contaminants from the solution to provide a first PEG supernatant containing Factor VIII;

(d) recovering the first PEG supernatant;

(e) adding additional precipitant consisting essentially of PEG to the first PEG supernatant to bring the PEG concentration to from about 8% to about 16% to thereby precipitate Factor VIII from the supernatant;

(f) recovering and then washing the Factor VIII precipitate in an aqueous solution containing (1) glycine at a concentration of from about 1 to about 2.6M, (2) citrate at a concentration of from about 0.1 to about 0.5M, and (3) heparin at a concentration of from about 10 to about 15 units of heparin per milliliter of solution, wherein the wash is maintained at less than about 15° C.; and (g) recovering the washed Factor VIII precipitate.

13. A process for producing a Factor VIII concentrate from blood plasma, the process comprising the steps of:

(a) obtaining a cryoprecipitate containing Factor VIII from blood plasma;

(b) dissolving the cryoprecipitate in an aqueous solution containing heparin in an amount sufficient to provide a cryoprecipitate/heparin solution containing about 80 units of heparin per milliliter of solution;

(c) adding a precipitant consisting essentially of PEG to the cryoprecipitate/heparin solution to provide a first solution having a PEG concentration of about 3% to 4% and adjusting the pH of the solution to about 6.3 to thereby precipitate unwanted protein contaminants from the solution to provide a first PEG supernatant containing Factor VIII;

(d) recovering the first PEG supernatant;

(e) adding additional precipitant consisting essentially of PEG to the first PEG supernatant to bring the PEG concentration to about 12% to thereby precipitate Factor VIII from the supernatant;

(f) recovering and then washing the Factor VIII precipitate in an aqueous solution containing (1) glycine at a concentration of about 1.6M, (2) citrate at a concentration of about 0.2M, and (3) heparin at a concentration of from about 10 to about 15 units of heparin per milliliter of solution, wherein the wash is maintained at less than about 15° C.; and (g) recovering the washed Factor VIII precipitate.

* * * * *